United States Patent [19]

Sponseller

[11] 4,425,802
[45] Jan. 17, 1984

[54] APPARATUS AND METHOD FOR TESTING TUBE WELDS

[75] Inventor: Harold P. Sponseller, Toledo, Ohio

[73] Assignee: Harold Sponseller and Associates, Inc., Toledo, Ohio

[21] Appl. No.: 380,224

[22] Filed: May 20, 1982

[51] Int. Cl.³ ............................................. G01N 3/08
[52] U.S. Cl. ........................................ 73/827; 73/850
[58] Field of Search ................. 73/827, 850, 788, 859

[56] References Cited

U.S. PATENT DOCUMENTS 4,358,961  11/1982  Woods ................................. 73/827

FOREIGN PATENT DOCUMENTS 418769  9/1974  U.S.S.R. ............................. 73/827

Primary Examiner—Anthony V. Ciarlante
Attorney, Agent, or Firm—E. J. Holler

[57] ABSTRACT

This invention relates to apparatus and method for testing tube welds, and more specifically the seams or joints of tubular metal pipe which may be tested rapidly and efficiently under mechanical load conditions which are applied stepwise.

12 Claims, 4 Drawing Figures

APPARATUS AND METHOD FOR TESTING TUBE WELDS

BACKGROUND OF THE INVENTION (1) Field of the Invention

The present invention relates to testing tubular materials and structures, and more particularly the seams or joints thereof which are tested under mechanical load comparable to service conditions.

(2) Description of the Prior Art

In the previous practice of testing butt welds, lap welds, and the like, at room temperature, a tubular specimen was mounted with one end secured rigidly in a suitable frame with the weld or seam to be tested adjacent a movable series of loose spherical balls or spheres adapted to contact the seam area. The spheres were only temporarily retained in sockets on a mandrel, and following considerable mechanical loading, tended to separate from the mandrel with great force upon breakage of the weld or seam area. In this practice, the series of spheres are moved simultaneously on and with the mandrel to place internal loading on the weld or seam area. As stated, upon breakage, such spheres tend to fly at random with explosive force creating a potential serious injury hazard. Shielding of such testing apparatus is normally required.

Another type of previous practice of testing welds, especially at elevated temperature and pressure, consisted of mounting the tubular specimen rigidly in a stationary frame in a manner such that the weld or seam to be tested was adjacent a fixed support. The opposite end of the specimen was then subjected to a bearing force of cyclical nature, normally in one plane of motion. Partial tests of tube welds were performed in this manner. However, the flexing action thus applied did not stress all portions of the weld accurately and did not reproduce service conditions of temperature and pressure simultaneously. Therefore, such weld tests previously made have been inadequate in determining the suitability of certain weld types for prescribed service usage.

Another type of apparatus for testing tube welds consists of a test stand for subjecting a tubular specimen to fatigue tests under repeated stressing of known loading amounts with the forces equally distributed on all sides of the cylindrical shape. This apparatus is adapted to duplicating in the tube welds similar severe conditions of temperature and pressure. Such apparatus is disclosed in U.S. Pat. No. 2,761,310 to Siegel, issued Sept. 4, 1956.

A still further type of device for weld testing is disclosed in U.S. Pat. No. 3,500,679 to Smith, issued Mar. 17, 1970. This device provides a test stand for bending the welded specimen into a substantially U-shape with anti-friction elements to assist in such bending.

The following additional patents pertain to testing welds in metals by various methods:

U.S. Pat. Nos. 1,200,086; 1,925,718; 2,002,552; 2,742,782; 2,776,695; 3,410,133; 3,636,758; 4,107,979.

SUMMARY OF THE INVENTION

This invention relates to apparatus and method for testing tube welds, and more specifically the seams or joints of tubular metal pipe which may be tested rapidly and efficiently under mechanical load conditions which are applied stepwise. The mechanical loading is safely applied to indicate threshold internal forces which the tubing is capable of retaining under loads comparable to service conditions. The apparatus employs a movable mandrel having a unitary member near its extremity comprising progressively larger bulbous portions adapted to penetrate and load the tubing internally. The bulbous portions have exterior surfaces which are generally spherical in contour to contact the internal surface of the weld. The increasingly larger bulbous portions permit stepwise loading of the tubing to a point where breakage will occur.

DESCRIPTION OF THE PREFERRED EMBODIMENT

Figure 1:
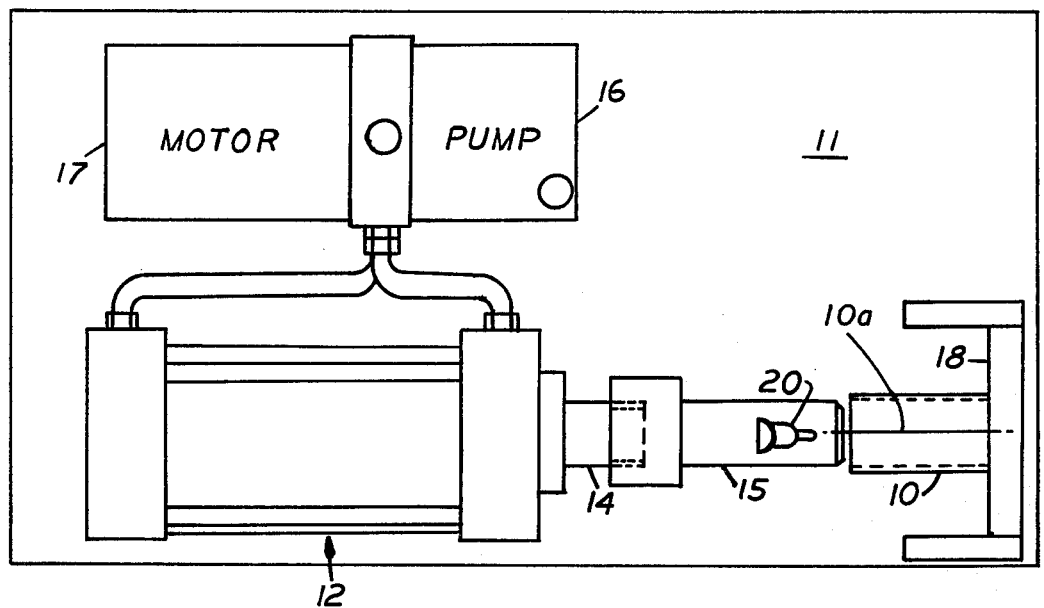
FIG. 1 is a top plan view of the material testing apparatus which embodies features of the present invention.
Figure 2:
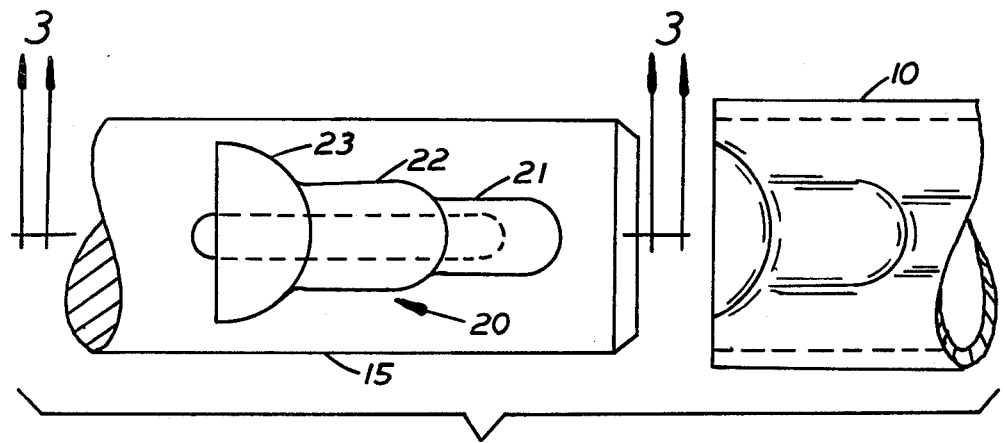
FIG. 2 is an enlarged fragmentary view of a portion of FIG. 1, showing the mandrel member and tubular test material of the apparatus.
Figure 3:
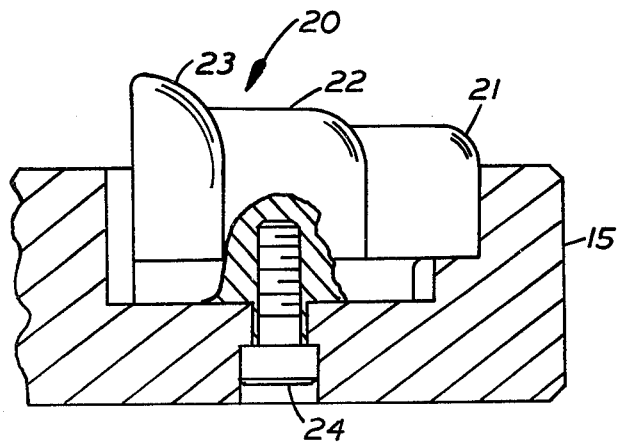
FIG. 3 is a further enlarged, vertical sectional view of the mandrel member of the apparatus taken along the line 3—3 of FIG. 2.
Figure 4:
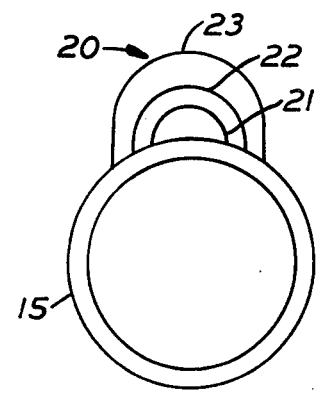
FIG. 4 is an end view of the mandrel member shown in FIG. 3 illustrating its working portion.

FIG. 1 shows a testing machine for a tubular material specimen 10 which comprises a base plate 11 having a hydraulic ram numeral 12 mounted thereon. The ram is comprised of a hollow cylinder 12 having a movable piston 14 therein on one end of which is mounted a mandrel member 15. The piston 14 is forcefully moved by hydraulic fluid supplied by a pump 16 and connecting motor 17. The pump is adapted to supply the hydraulic cylinder with fluid at increased pressure for powering mandrel member 15 forwardly into extended position in a conventional manner, without rotation.

In accordance with the present invention, test specimen 10 consists of a short length of tubular material which is normally metal having a lineal seam 10a in the form of a butt weld, lap weld or other type of weld or joint. The specimen is placed in co-axial alignment with mandrel member 15. The end of the specimen is placed in stationary relation against a fixed vertical crosshead 18, having the form of a stationary flat vertical plate. The faces of such plate and the specimen are mounted in co-planar facing relation to ensure uniform loading of the specimen.

The mandrel member 15 of the apparatus is movable having a unitary member 20 mounted fixedly on a cylindrical segment thereof. The unitary member 20 has a lineal series so progressively-larger rigid bulbous portions 21, 22 and 23 which are located near the cantilevered extremity of mandrel member 15. The unitary member 20 may be affixed to a slot in the mandrel by a bolt 24 extending from the opposite side of the mandrel in countersunk relation. The specimen 10 is placed with its weld portion in lineal alignment with the rigid bulbous portions of the unitary member. The smallest bulbous portion 21 in conjunction with the remainder of the mandrel normally provides a slightly larger diameter than the internal diameter of the tubular specimen to be tested. The bulbous portions affixed in rigid stationary relation on the mandrel have a generally-spherical exterior contour to present a ball-shaped configuration to the internal surface of the weld or joint. Such application of forces serves to stress the weld or joint by straining in circumferential tension from within, usually resulting in stretching of same to the point of fracture.

When the apparatus is employed to test a specimen by tension, the hydraulic pump is energized to move the mandrel and the unitary member 20 into the open end of the specimen. The bulbous portions 21, 22 and 23 serve to impart stepwise tensile loading on the weld area of the specimen from an inner direction outwardly. The bulbous portions thus exert stepwise loading on the specimen to a threshold at which breakage will occur. The action generated provides a substantial mechanical advantage according to the common principles of wedge action. There is no opportunity for the bulbous portions to separate from the fixed unitary member on specimen breakage and no possibility of specimen slippage. Also geometric strain produced is accurately repeatable.

The fixed unitary member provides means for applying the loading to the specimen slowly and positively. The bulbous portions being comprised of a single durable member provide a safety feature. While some flow of the metal of the weld area does occur immediately prior to breakage on increased loading, the bulbous portions permit a prescribed form of classifying the strength of the specimen tested, and cannot separate from the mandrel in an uncontrolled manner. The specimen may be classified as capable of withstanding two or more levels of loading, since the bulbous portions may number 2, 3, 4 or more in making up the unitary member. The slowly increasing compressive force supplied by the mandrel permits determination of the stress, deformation and breaking strength of the tube seam area.

Various modifications may be resorted to within the spirit and scope of the appended claims.

I claim:

1. A device for testing joints in a rigid tubular material comprising a first fixture means for supporting a fixed first end of said tubular material, second fixture means contacting a non-fixed second end of said material, said second fixture means having a movable mandrel member and a lineal series of progressively-larger rigid bulbous portions adjacent the extremity of said mandrel member adapted to engage the seam area of said material and means for progressively loading the said second fixture means with increasing axial force to determine the breaking strength of said seam area by the increased stepwise radial loading thereof by the rigid bulbous portions.

2. The device in accordance with claim 1, wherein said second fixture means includes a plurality of progressively-larger bulbous portions adapted to penetrate and contact the seam area of said material.

3. The device in accordance with claim 1, wherein said second fixture means includes a series of three progressively-larger rigid bulbous portions mounted on said movable mandrel adapted to penetrate and progressively loading the seam area of said material.

4. The device in accordance with claim 1, wherein the said means for progressively loading the said second fixture means comprises a hydraulic ram.

5. The device in accordance with claim 1, wherein the said series of progressively-larger rigid bulbous portions is disposed in coaxial alignment with the said seam area of said movable mandrel member.

6. The device in accordance with claim 2, wherein the said plurality of progressively-larger rigid bulbous portions have an increasing diameter in a direction away from the extremity of said movable mandrel member.

7. The device in accordance with claim 3, wherein the said series of three progressively-larger rigid bulbous portions is co-axially aligned with and adapted to deliver increased stepwise loading stress to the seam area of said material.

8. The device in accordance with claim 1, wherein the said series of rigid bulbous portions is comprised of an integral unitary member affixed to a localized region of said movable mandrel member.

9. A device for testing joints such as welds in a rigid tubular material comprising a first fixture means for supporting a fixed first end of said tubular material, second fixture means contacting a non-fixed second end of said material, said second fixture means comprising a movable mandrel member having a series of three rigid bulbous portions which are progressively-larger in a direction away from the extremity of said mandrel member and located adjacent said extremity adapted to engage the joint area of said material, and means for progressively loading the said second fixture means with increasing mandrel axial force to determine the breaking strength of said joint area by the increased radial loading stepwise by the rigid bulbous portions.

10. The method of testing joints such as welds in a rigid tubular material comprising the steps of supporting a first end of said material in stationary relation, mounting a second end of said material in non-fixed relation, inserting a movable mandrel member into the non-fixed end of said material said movable mandrel member having a lineal series of progressively-larger rigid bulbous portions adjacent its extremity, aligning said series of rigid bulbous portions in co-axial alignment with the seam area of said material, and applying slowly increasing compressive force to said mandrel member to determine the stress, deformation and breaking strength of said seam area by the increased stepwise loading by the rigid bulbous portions.

11. The method in accordance with claim 10, including the step of slowly progressively loading the said material with said movable mandrel member to determine the breaking strength of said seam area.

12. The method in accordance with claim 10, including the step of applying the said increasing axial force with the said rigid bulbous portions being comprised of an integral unitary member affixed adjacent to the extremity of said mandrel member.

* * * * *